(12) United States Patent
Bell et al.

(10) Patent No.: US 8,080,544 B2
(45) Date of Patent: Dec. 20, 2011

(54) PRODRUGS OF CGRP RECEPTOR ANTAGONISTS

(75) Inventors: Ian M. Bell, Harleysville, PA (US); Steven N. Gallicchio, Horsham, PA (US); Valentino J. Stella, Lawrence, KS (US)

(73) Assignee: Merck Sharp & Dohme Corp., Rahway, NJ (US)

( * ) Notice: Subject to any disclaimer, the term of this patent is extended or adjusted under 35 U.S.C. 154(b) by 0 days.

(21) Appl. No.: 12/864,120

(22) PCT Filed: Feb. 4, 2009

(86) PCT No.: PCT/US2009/033008
§ 371 (c)(1),
(2), (4) Date: Jul. 22, 2010

(87) PCT Pub. No.: WO2009/100090
PCT Pub. Date: Aug. 13, 2009

(65) Prior Publication Data
US 2010/0298269 A1    Nov. 25, 2010

Related U.S. Application Data

(60) Provisional application No. 61/063,656, filed on Feb. 5, 2008.

(51) Int. Cl.
*A61K 31/55* (2006.01)
*A61P 25/06* (2006.01)
*C07D 471/04* (2006.01)

(52) U.S. Cl. .................. 514/212.07; 540/487
(58) Field of Classification Search .................. 540/487; 514/212.07
See application file for complete search history.

(56) References Cited

U.S. PATENT DOCUMENTS

| | | | |
|---|---|---|---|
| 6,953,790 B2 | 10/2005 | Burgey et al. | |
| 7,235,545 B2 | 6/2007 | Burgey et al. | |
| 7,452,903 B2 | 11/2008 | Burgey et al. | |
| 7,534,784 B2 | 5/2009 | Burgey et al. | |
| 7,718,796 B2 | 5/2010 | Palucki et al. | |
| 2007/0225272 A1 | 9/2007 | Burgey et al. | |
| 2007/0287696 A1 | 12/2007 | Burgey et al. | |
| 2007/0287697 A1 | 12/2007 | Paone et al. | |
| 2009/0192139 A1 | 7/2009 | Paone et al. | |
| 2009/0281306 A1 | 11/2009 | Belyk et al. | |
| 2010/0009967 A1 | 1/2010 | Mahjour et al. | |

FOREIGN PATENT DOCUMENTS

| | | |
|---|---|---|
| WO | 2004092168 | 10/2004 |
| WO | 2007120591 | 10/2007 |
| WO | 2007120592 | 10/2007 |

OTHER PUBLICATIONS

Co-pending U.S. Appl. No. 12/086,670, filed Jun. 13, 2008.
Co-pending U.S. Appl. No. 12/310,808, filed Mar. 6, 2009.
Co-pending U.S. Appl. No. 12/831,802, filed Jul. 7, 2010.
Supplementary European Search Report and Search Opinion for counterpart European patent application No. EP 09 70 8648.

*Primary Examiner* — Bruck Kifle
(74) *Attorney, Agent, or Firm* — Gerard M. Devlin; Raynard Yuro

(57) ABSTRACT

Disclosed are prodrug compounds of formula (I) (wherein variables $R^1$ and $R^2$ are as described herein) which are analogues of an antagonist of CGRP receptors and which are useful in the treatment or prevention of diseases in which CGRP is involved, such as migraine. The invention is also directed to pharmaceutical compositions comprising these compounds and the use of these compounds and compositions in the prevention or treatment of such diseases in which CGRP is involved.

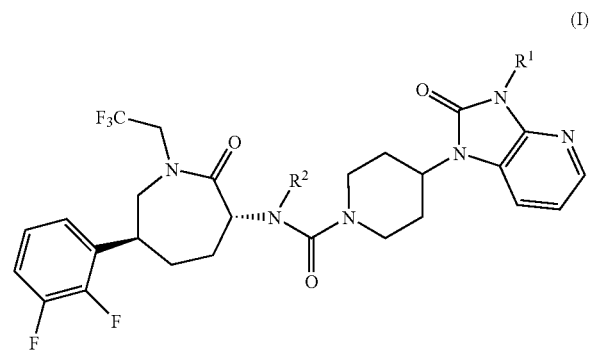

(I)

5 Claims, No Drawings

PRODRUGS OF CGRP RECEPTOR ANTAGONISTS

FIELD OF THE INVENTION

The invention is directed to prodrugs of the CGRP receptor antagonist N-[(3R,6S)-6-(2,3-difluorophenyl)-2-oxo-1-(2,2,2-trifluoroethyl)azepan-3-yl]-4-(2-oxo-2,3-dihydro-1H-imidazo[4,5-b]pyridine-1-yl)piperidin-1-carboxamide (Compound 1), and pharmaceutically acceptable salts thereof. The invention is also directed to methods of treating diseases or disorders that involve CGRP, such as migraine and cluster headache.

BACKGROUND OF THE INVENTION

CGRP (Calcitonin Gene-Related Peptide) is a naturally occurring 37-amino acid peptide that is generated by tissue-specific alternate processing of calcitonin messenger RNA and is widely distributed in the central and peripheral nervous system. CGRP is localized predominantly in sensory afferent and central neurons and mediates several biological actions, including vasodilation. CGRP is expressed in alpha- and beta-forms that vary by one and three amino acids in the rat and human, respectively. CGRP-alpha and CGRP-beta display similar biological properties. When released from the cell, CGRP initiates its biological responses by binding to specific cell surface receptors that are predominantly coupled to the activation of adenylyl cyclase. CGRP receptors have been identified and pharmacologically evaluated in several tissues and cells, including those of brain, cardiovascular, endothelial, and smooth muscle origin.

Based on pharmacological properties, these receptors are divided into at least two subtypes, denoted $CGRP_1$ and $CGRP_2$. Human α-CGRP-(8-37), a fragment of CGRP that lacks seven N-terminal amino acid residues, is a selective antagonist of $CGRP_1$, whereas the linear analogue of CGRP, diacetoamido methyl cysteine CGRP ([Cys(ACM)2,7] CGRP), is a selective agonist of $CGRP_2$. CGRP is a potent neuromodulator that has been implicated in the pathology of cerebrovascular disorders such as migraine and cluster headache. In clinical studies, elevated levels of CGRP in the jugular vein were found to occur during migraine attacks (Goadsby et al., Ann. Neurol., 1990, 28, 183-187), and salivary levels of CGRP were shown to be elevated in migraine subjects between attacks (Bellamy et al., Headache, 2006, 46, 24-33). CGRP itself has been shown to trigger migrainous headache (Lassen et al., Cephalalgia, 2002, 22, 54-61). In clinical trials, the CGRP antagonist BIBN4096BS has been shown to be effective in treating acute attacks of migraine (Olesen et al., New Engl. J. Med., 2004, 350, 1104-1110) and was able to prevent headache induced by CGRP infusion in a control group (Petersen et al., Clin. Pharmacol. Ther., 2005, 77, 202-213).

CGRP-mediated activation of the trigeminovascular system may play a key role in migraine pathogenesis. Additionally, CGRP activates receptors on the smooth muscle of intracranial vessels, leading to increased vasodilation, which is thought to contribute to headache pain during migraine attacks (Lance, Headache Pathogenesis: Monoamines, Neuropeptides, Purines and Nitric Oxide, Lippincott-Raven Publishers, 1997, 3-9). The middle meningeal artery, the principle artery in the dura mater, is innervated by sensory fibers from the trigeminal ganglion which contain several neuropeptides, including CGRP. Trigeminal ganglion stimulation in the cat resulted in increased levels of CGRP, and in humans, activation of the trigeminal system caused facial flushing and increased levels of CGRP in the external jugular vein (Goadsby et al., Ann. Neurol., 1988, 23, 193-196). Electrical stimulation of the dura mater in rats increased the diameter of the middle meningeal artery, an effect that was blocked by prior administration of CGRP(8-37), a peptide CGRP antagonist (Williamson et al., Cephalalgia, 1997, 17, 525-531). Trigeminal ganglion stimulation increased facial blood flow in the rat, which was inhibited by CGRP(8-37) (Escott et al., Brain Res. 1995, 669, 93-99). Electrical stimulation of the trigeminal ganglion in marmoset produced an increase in facial blood flow that could be blocked by the non-peptide CGRP antagonist BIBN4096BS (Doods et al., Br. J. Pharmacol., 2000, 129, 420-423). Thus the vascular effects of CGRP may be attenuated, prevented or reversed by a CGRP antagonist.

CGRP-mediated vasodilation of rat middle meningeal artery was shown to sensitize neurons of the trigeminal nucleus caudalis (Williamson et al., The CGRP Family: Calcitonin Gene-Related Peptide (CGRP), Amylin, and Adrenomedullin, Landes Bioscience, 2000, 245-247). Similarly, distention of dural blood vessels during migraine headache may sensitize trigeminal neurons. Some of the associated symptoms of migraine, including extra-cranial pain and facial allodynia, may be the result of sensitized trigeminal neurons (Burstein et al., Ann. Neurol. 2000, 47, 614-624). A CGRP antagonist may be beneficial in attenuating, preventing or reversing the effects of neuronal sensitization.

The ability of the compounds of the present invention to act as CGRP antagonists makes them useful pharmacological agents for disorders that involve CGRP in humans and animals, but particularly in humans. Such disorders include migraine and cluster headache (Doods, Curr Opin Inves Drugs, 2001, 2 (9), 1261-1268; Edvinsson et al., Cephalalgia, 1994, 14, 320-327); chronic tension type headache (Ashina et al., Neurology, 2000, 14, 1335-1340); pain (Yu et al., Eur. J. Pharm., 1998, 347, 275-282); chronic pain (Hulsebosch et al., Pain, 2000, 86, 163-175); neurogenic inflammation and inflammatory pain (Holzer, Neurosci., 1988, 24, 739-768; Delay-Goyet et al., Acta Physiol. Scanda. 1992, 146, 537-538; Salmon et al., Nature Neurosci., 2001, 4(4), 357-358); eye pain (May et al. Cephalalgia, 2002, 22, 195-196); tooth pain (Awawdeh et al., Int. Endocrin. J., 2002, 35, 30-36); non-insulin dependent diabetes mellitus (Molina et al., Diabetes, 1990, 39, 260-265); vascular disorders; inflammation (Zhang et al., Pain, 2001, 89, 265); arthritis, bronchial hyperreactivity, asthma (Foster et al., Ann. NY Acad. Sci., 1992, 657, 397-404; Schini et al., Am. J. Physiol., 1994, 267, H2483-H2490; Zheng et al., J. Virol., 1993, 67, 5786-5791); shock, sepsis (Beer et al., Crit. Care Med., 2002, 30 (8), 1794-1798); opiate withdrawal syndrome (Salmon et al., Nature Neurosci., 2001, 4(4), 357-358); morphine tolerance (Menard et al., J. Neurosci., 1996, 16 (7), 2342-2351); hot flashes in men and women (Chen et al., Lancet, 1993, 342, 49; Spetz et al., J. Urology, 2001, 166, 1720-1723); allergic dermatitis (Wallengren, Contact Dermatitis, 2000, 43 (3), 137-143); psoriasis; encephalitis, brain trauma, ischaemia, stroke, epilepsy, and neurodegenerative diseases (Rohrenbeck et al., Neurobiol. of Disease 1999, 6, 15-34); skin diseases (Geppetti and Holzer, Eds., Neurogenic Inflammation, 1996, CRC Press, Boca Raton, Fla.); neurogenic cutaneous redness, skin rosaceousness and erythema; tinnitus (Herzog et al., J. Membrane Biology, 2002, 189(3), 225); inflammatory bowel disease, irritable bowel syndrome, (Hoffman et al. Scandinavian Journal of Gastroenterology, 2002, 37(4) 414-422) and cystitis. Of particular importance is the acute or prophylactic treatment of headache, including migraine and cluster headache.

The CGRP receptor antagonist N-[(3R,6S)-6-(2,3-difluorophenyl)-2-oxo-1-(2,2,2-trifluoroethyl)azepan-3-yl]-4-(2-oxo-2,3-dihydro-1H-imidazo[4,5-b]pyridine-1-yl)piperidin-1-carboxamide (telcagepant)

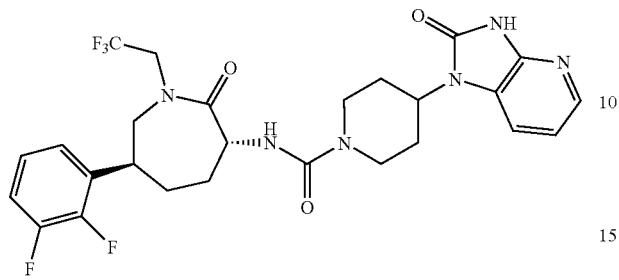

and pharmaceutically acceptable salts thereof, is disclosed in International Application No. WO04/092166, published Oct. 28, 2004. Various salt and solvate forms of telcagepant are described in International Application No. WO 2007/120592, published Oct. 25, 2007.

Telcagepant is currently in clinical development for the acute treatment of migraine. However, telcagepant has demonstrated a low aqueous solubility, and this has made it difficult to formulate for certain methods of dosing (for example, as an injectable). A water-soluble prodrug of telcagepant could potentially solve this problem by allowing for an aqueous formulation that would be rapidly converted to parent drug in vivo.

Further, in the clinical setting it is desirable to have a variety of dosing options for a migraine therapy, including tablets or capsules for oral administration and injectable formulations. One strategy for expanding the range of dosing options is to make use of prodrugs of the parent compound. Such prodrugs may offer advantages such as enhanced oral absorption or improved physical properties. For example, a water-soluble prodrug of telcagepant could potentially facilitate the development of an aqueous formulation that would be rapidly converted to parent drug in vivo.

SUMMARY OF THE INVENTION

The present invention is directed to compounds of the formula I:

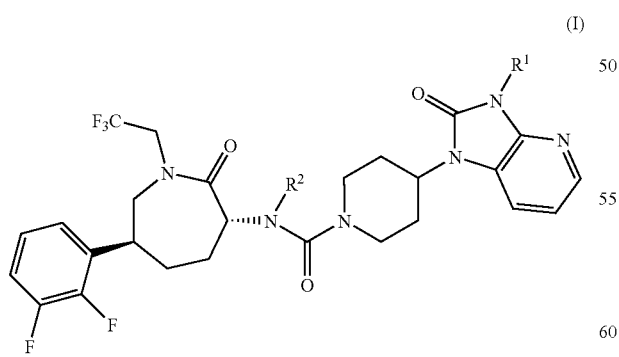

(wherein variables $R^1$ and $R^2$ are as described herein) which are analogues of an antagonist of CGRP receptors and which are useful as prodrugs in the treatment or prevention of diseases in which CGRP is involved, such as migraine. The invention is also directed to pharmaceutical compositions comprising these compounds and the use of these compounds and compositions in the prevention or treatment of such diseases in which CGRP is involved.

DETAILED DESCRIPTION OF THE INVENTION

The present invention is directed to compounds of the formula I:

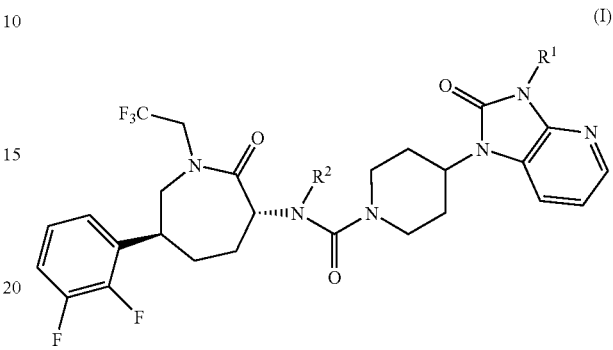

wherein:
$R^1$ is selected from:
(1) hydrogen,
(2) $C_{1-6}$alkyl, which is unsubstituted or substituted with 1-7 substituents each independently selected from:
  (a) halo,
  (b) —$OR^a$,
  (c) —$OP(=O)(OR^b)_2$,
  (d) —$OP(=O)(OR^b)R^a$,
  (e) —$OP(=O)R^aR^b$,
  (f) —$OP(=O)(OR^b)$—$OP(=O)(OR^b)_2$,
  (g) —$C_{3-6}$cycloalkyl, which is unsubstituted or substituted with 1-5 halo,
  (h) —CN,
  (i) phenyl or heterocycle wherein said heterocycle is selected from pyridyl, pyrimidinyl, thienyl, pyridazinyl, piperidinyl, azetidinyl, furanyl, piperazinyl, pyrrolidinyl, morpholinyl, tetrahydrofuranyl, tetrahydropyranyl and pyrazinyl, which phenyl or heterocycle is unsubstituted or substituted with 1-3 substituents each independently selected from:
    (i) halo,
    (ii) —O—$C_{1-6}$alkyl, which is unsubstituted or substituted with 1-6 halo,
    (iii) —CN,
    (iv) nitro,
    (v) hydroxyl, and
    (vi) —$C_{1-6}$alkyl, which is unsubstituted or substituted with 1-6 halo,
  (j) —$NR^bR^c$,
  (k) —$S(O)_vR^d$,
  (l) —$C(=O)NR^bR^c$,
  (m) —$NR^b$—$C(=O)R^a$,
  (n) —$NR^b$—$SO_2R^d$,
  (O) —O—$CO_2R^d$,
  (p) —O—(C=O)—$NR^bR^c$,
  (q) —$NR^b$—(C=O)—$NR^bR^c$,
  (r) —$C(=O)R^a$,
  (s) —$CO_2R^a$,
  (t) —O—$C(=O)R^a$,
  (u) —$NR^b$—$CO_2R^d$,
  (v) —$NR^b$—(C=$NR^b$)—$NR^bR^c$, and
  (w) —$CF_3$, (3) —C$_{3-6}$cycloalkyl, which is unsubstituted or substituted with 1-4 substituents each independently selected from:
  (a) halo,
  (b) —CN,
  (c) —O—C$_{1-6}$alkyl, which is unsubstituted or substituted with 1-6 halo,
  (d) hydroxyl, and
  (e) —C$_{1-6}$alkyl, which is unsubstituted or substituted with 1-6 halo, and
(4) —C(=O)R$^a$;

R$^2$ is selected from:
(1) hydrogen,
(2) C$_{1-6}$alkyl, which is substituted with 1-7 substituents each independently selected from:
  (a) —OP(=O)(OR$^b$)$_2$,
  (b) —OP(=O)(OR$^b$)R$^a$,
  (c) —OP(=O)R$^a$R$^b$,
  (d) —OP(=O)(OR$^b$)—OP(=O)(OR)$_2$,
  (e) —CN,
  (g) —NR$^b$R$^c$,
  (h) —S(O)$_v$R$^d$,
  (i) —C(=O)NR$^b$R$^c$,
  (j) —NR$^b$—C(=O)R$^a$,
  (k) —NR$^b$—SO$_2$R$^d$,
  (l) —O—CO$_2$R$^d$,
  (m) —O—(C=O)—NR$^b$R$^c$,
  (n) —NR$^b$—(C=O)—NR$^b$R$^c$,
  (o) —C(=O)R$^a$,
  (p) —CO$_2$R$^a$,
  (q) —O—C(=O)R$^a$,
  (r) —NR$^b$—CO$_2$R$^d$, and
  (s) —NR$^b$—(C=NR$^b$)—NR$^b$R$^c$, and
(3) —C(=O)R$^a$;

wherein no more than one of R$^1$ and R$^2$ is hydrogen;

R$^a$ is independently selected from:
(1) hydrogen,
(2) C$_{1-6}$alkyl, which is unsubstituted or substituted with 1-7 substituents each independently selected from:
  (a) halo,
  (b) —O—C$_{1-6}$alkyl, which is unsubstituted or substituted with 1-6 halo,
  (c) hydroxyl,
  (d) —CN,
  (e) phenyl or heterocycle wherein said heterocycle is selected from pyridyl, pyrimidinyl, thienyl, pyridazinyl, piperidinyl, azetidinyl, furanyl, piperazinyl, pyrrolidinyl, morpholinyl, tetrahydrofuranyl, tetrahydropyranyl and pyrazinyl, which phenyl or heterocycle is unsubstituted or substituted with 1-3 substituents each independently selected from:
    (i) halo,
    (ii) —O—C$_{1-6}$alkyl, which is unsubstituted or substituted with 1-6 halo,
    (iii) —CN,
    (iv) nitro,
    (v) hydroxyl, and
    (vi) —C$_{1-6}$alkyl, which is unsubstituted or substituted with 1-6 halo,
  (f) C$_{3-6}$cycloalkyl, which is unsubstituted or substituted with 1-5 substituents each independently selected from:
    (i) halo,
    (ii) which is unsubstituted or substituted with 1-6 halo,
    (iii) —CN,
    (iv) hydroxyl, and
    (v) —C$_{1-6}$alkyl, which is unsubstituted or substituted with 1-6 halo,
  (g) —NR$^b$R$^c$,
  (h) —S(O)$_v$R$^d$,
  (i) —C(=O)NR$^b$R$^c$,
  (j) —NR$^b$—C(=O)R$^c$,
  (k) —NR$^b$—SO$_2$R$^d$,
  (l) —O—CO$_2$R$^d$,
  (m) —O—(C=O)—NR$^b$R$^c$,
  (n) —NR$^b$—(C=O)—NR$^b$R$^c$,
  (o) —C(=O)R$^b$,
  (p) —CO$_2$R$^b$,
  (q) —O—C(=O)R$^b$,
  (r) —NR$^b$—CO$_2$R$^d$,
  (s) —NR$^b$—(C=NR$^b$)—NR$^b$R$^c$,
  (t) —CF$_3$,
  (u) —Si(C$_{1-4}$alkyl)$_3$, and
  (v) —OP(=O)(OR$^b$)$_2$, and
(3) phenyl or heterocycle wherein said heterocycle is selected from pyridyl, pyrimidinyl, thienyl, pyridazinyl, piperidinyl, azetidinyl, furanyl, piperazinyl, pyrrolidinyl, morpholinyl, tetrahydrofuranyl, tetrahydropyranyl and pyrazinyl, which phenyl or heterocycle is unsubstituted or substituted with 1-3 substituents each independently selected from:
  (a) halo,
  (b) —CN,
  (c) —O—C$_{2-6}$alkyl, which is unsubstituted or substituted with 1-6 halo,
  (d) nitro,
  (e) hydroxyl, and
  (f) —C$_{1-6}$alkyl, which is unsubstituted or substituted with 1-6 halo, and
(4) —C$_{3-6}$cycloalkyl, which is unsubstituted or substituted with 1-6 halo;

R$^b$ and R$^c$ are independently selected from:
(1) hydrogen,
(2) C$_{1-6}$alkyl, which is unsubstituted or substituted with 1-7 substituents each independently selected from:
  (a) halo,
  (b) hydroxyl,
  (c) —O—C$_{1-6}$alkyl, which is unsubstituted or substituted with 1-6 halo,
  (d) —CN,
  (e) —CO$_2$R$^d$,
  (f) phenyl or heterocycle, wherein said heterocycle is selected from pyridyl, pyrimidinyl, thienyl, pyridazinyl, piperidinyl, azetidinyl, furanyl, piperazinyl, pyrrolidinyl, morpholinyl, tetrahydrofuranyl, tetrahydropyranyl and pyrazinyl, which phenyl or heterocycle is unsubstituted or substituted with 1-3 substituents each independently selected from:
    (i) halo,
    (ii) —O—C$_{1-6}$alkyl, which is unsubstituted or substituted with 1-6 halo,
    (iii) —C$_{1-6}$alkyl, which is unsubstituted or substituted with 1-6 halo, and
    (iv) hydroxyl,
(3) phenyl or heterocycle, wherein said heterocycle is selected from pyridyl, pyrimidinyl, thienyl, pyridazinyl, piperidinyl, azetidinyl, furanyl, piperazinyl, pyrrolidinyl, morpholinyl, tetrahydrofuranyl, tetrahydropyranyl and pyrazinyl, which phenyl or heterocycle is unsubstituted or substituted with 1-3 substituents each independently selected from:

(a) halo,
(b) —O—$C_{1-6}$alkyl, which is unsubstituted or substituted with 1-6 halo,
(c) hydroxyl,
(d) —$C_{1-6}$alkyl, which is unsubstituted or substituted with 1-6 halo,
(e) —$C_{3-6}$cycloalkyl, which is unsubstituted or substituted with 1-6 halo,
(f) —CN, and
(g) —$CO_2R^d$,
(4) —$C_{3-6}$cycloalkyl, which is unsubstituted or substituted with 1-6 halo;
or $R^b$ and $R^c$ and the nitrogen to which they are attached join to form a 4-, 5-, or 6-membered ring optionally containing an additional heteroatom selected from N, O, and S, wherein the sulfur is optionally oxidized to the sulfone or sulfoxide, which ring is unsubstituted or substituted with 1-4 substituents each independently selected from:
(a) halo,
(b) —$OR^d$,
(c) —$C_{1-6}$alkyl, which is unsubstituted or substituted with 1-6 halo, and
(d) phenyl;
$R^d$ is independently selected from:
  (1) $C_{1-6}$alkyl, which is unsubstituted or substituted with 1-4 substituents each independently selected from:
    (a) halo,
    (b) —O—$C_{1-6}$alkyl, which is unsubstituted or substituted with 1-6 halo,
    (c) hydroxyl,
    (d) —$CO_2$—$C_{1-4}$alkyl,
    (e) —$CO_2H$,
    (f) —CN, and
    (g) phenyl or heterocycle, wherein said heterocycle is selected from pyridyl, pyrimidinyl, thienyl, pyridazinyl, piperidinyl, azetidinyl, furanyl, piperazinyl, pyrrolidinyl, morpholinyl, tetrahydrofuranyl, tetrahydropyranyl and pyrazinyl, which phenyl or heterocycle is unsubstituted or substituted with 1-3 substituents each independently selected from:
      (i) halo,
      (ii) —O—$C_{1-6}$alkyl, which is unsubstituted or substituted with 1-6 halo,
      (iii) —$C_{1-6}$alkyl, which is unsubstituted or substituted with 1-6 halo, and
      (iv) hydroxyl,
  (2) phenyl or heterocycle, wherein said heterocycle is selected from pyridyl, pyrimidinyl, thienyl, pyridazinyl, piperidinyl, azetidinyl, furanyl, piperazinyl, pyrrolidinyl, morpholinyl, tetrahydrofuranyl, tetrahydropyranyl and pyrazinyl, which phenyl or heterocycle is unsubstituted or substituted with 1-3 substituents each independently selected from:
    (a) halo,
    (b) —O—$C_{1-6}$alkyl, which is unsubstituted or substituted with 1-6 halo,
    (c) hydroxyl,
    (d) —$C_{1-6}$alkyl, which is unsubstituted or substituted with 1-6 halo,
    (e) —$C_{3-6}$cycloalkyl, which is unsubstituted or substituted with 1-6 halo,
    (f) —CN,
    (g) —$CO_2$—$C_{1-4}$alkyl, and
    (h) —$CO_2H$, and
  (3) —$C_{3-6}$cycloalkyl, which is unsubstituted or substituted with 1-6 halo;
v is 0, 1, or 2;
and pharmaceutically acceptable salts thereof and individual enantiomers and diastereomers thereof.

An embodiment of the present invention includes compounds of the formula Ia:

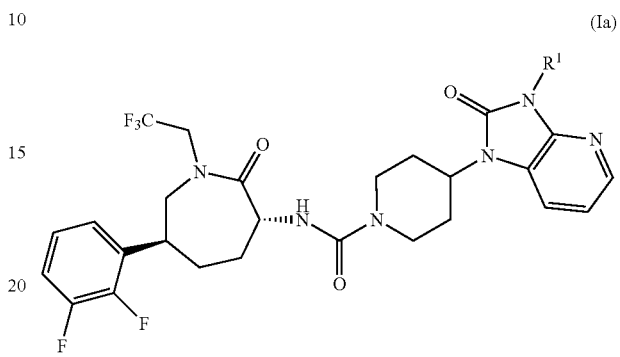

(Ia)

wherein $R^1$ is defined herein;
and pharmaceutically acceptable salts thereof and individual enantiomers and diastereomers thereof.

Another embodiment of the present invention includes compounds of the formula Ib:

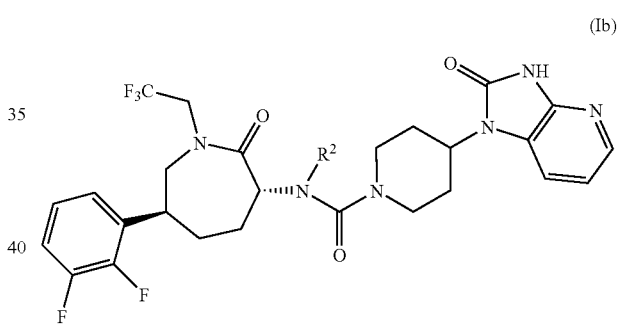

(Ib)

wherein $R^2$ is defined herein;
and pharmaceutically acceptable salts thereof and individual enantiomers and diastereomers thereof.

In an embodiment of the present invention $R^1$ is selected from:
(1) hydrogen,
(2) $C_{1-6}$alkyl, which is unsubstituted or substituted with 1-5 substituents each independently selected from:
  (a) halo,
  (b) —$OR^a$,
  (c) —OP(=O)$(OR^b)_2$,
  (d) —OP(=O)$(OR^b)R^a$,
  (e) —OP(=O)$R^aR^b$,
  (f) —$C_{3-6}$cycloalkyl,
  (g) phenyl or heterocycle wherein said heterocycle is selected from pyridyl, pyrimidinyl, piperidinyl, piperazinyl, pyrrolidinyl, morpholinyl, and tetrahydrofuranyl, which phenyl or heterocycle is unsubstituted or substituted with 1-3 substituents each independently selected from:
    (i) halo,
    (ii) —O—$C_{1-4}$alkyl,
    (iii) —CN, (iv) hydroxyl, and
(v) —$C_{1-4}$alkyl, which is unsubstituted or substituted with 1-3 halo,
(h) —$NR^bR^c$,
(i) —O—$CO_2R^d$,
(j) —$CO_2R^a$, and
(k) —O—C(=O)$R^a$, and
(3) —C(=O)$R^a$.

and pharmaceutically acceptable salts thereof and individual enantiomers and diastereomers thereof.

In an embodiment of the present invention $R^1$ is selected from:
(1) hydrogen, and
(2) $C_{1-4}$alkyl, which is unsubstituted or substituted with 1-3 substituents each independently selected from:
(a) halo,
(b) —$OR^a$,
(c) —OP(=O)$(OR^b)_2$,
(d) —OP(=O)$(OR^b)R^a$,
(e) —$C_{3-6}$cycloalkyl,
(f) phenyl,
(g) —$NR^bR^c$,
(h) —O—$CO_2R^d$,
(i) —$CO_2R^a$, and
(j) —O—C(=O)$R^a$, and pharmaceutically acceptable salts thereof and individual enantiomers and diastereomers thereof.

In an embodiment of the present invention $R^1$ is selected from:
(1) hydrogen, and
(2) $C_{1-4}$alkyl, which is unsubstituted or substituted with 1-3 substituents each independently selected from:
(a) halo,
(b) —OP(=O)$(OR^b)_2$,
(c) —OP(=O)$(OR^b)R^a$,
(d) —$C_{3-6}$cycloalkyl,
(e) phenyl, and pharmaceutically acceptable salts thereof and individual enantiomers and diastereomers thereof.

In an embodiment of the present invention $R^1$ is selected from:
(1) hydrogen, and
(2) $C_{1-4}$alkyl, which is unsubstituted or substituted with 1-2 substituents each independently selected from:
(a) —OP(=O)$(OH)_2$,
(b) —OP(=O)(OH)$R^a$, and pharmaceutically acceptable salts thereof and individual enantiomers and diastereomers thereof.

In an embodiment of the present invention $R^2$ is selected from:
(1) hydrogen,
(2) $C_{1-6}$alkyl, which is substituted with 1-5 substituents each independently selected from:
(a) —OP(=O)$(OR^b)_2$,
(b) —OP(=O)$(OR^b)R^a$,
(c) —OP(=O)$R^aR^b$,
(d) —$NR^bR^e$,
(e) —O—$CO_2R^d$,
(f) —$CO_2R^a$, and
(g) —O—C(=O)$R^a$, and
(3) —C(=O)$R^a$, and pharmaceutically acceptable salts thereof and individual enantiomers and diastereomers thereof.

In an embodiment of the present invention $R^2$ is selected from:
(1) hydrogen, and
(2) $C_{1-4}$alkyl, which is substituted with 1-3 substituents each independently selected from:
(a) —OP(=O)$(OR^b)_2$,
(b) —OP(=O)$(OR^b)R^a$, and
(c) —OP(=O)$R^aR^b$, and pharmaceutically acceptable salts thereof and individual enantiomers and diastereomers thereof.

In an embodiment of the present invention $R^2$ is selected from:
(1) hydrogen, and
(2) $C_{1-4}$alkyl, which is substituted with 1-3 substituents, wherein each is —OP(=O)$(OH)_2$, and pharmaceutically acceptable salts thereof and individual enantiomers and diastereomers thereof.

In an embodiment of the present invention $R^a$ is independently selected from:
(1) hydrogen,
(2) $C_{1-4}$alkyl, which is unsubstituted or substituted with 1-5 substituents each independently selected from:
(a) halo,
(b) —O—$C_{1-4}$alkyl, which is unsubstituted or substituted with 1-3 halo,
(c) hydroxyl,
(d) phenyl or heterocycle wherein said heterocycle is selected from pyridyl, pyrimidinyl, piperidinyl, piperazinyl, pyrrolidinyl, morpholinyl, and tetrahydrofuranyl, which phenyl or heterocycle is unsubstituted or substituted with 1-3 substituents each independently selected from:
(i) halo,
(ii) —O—$C_{1-4}$alkyl,
(iii) —CN,
(iv) hydroxyl, and
(v) which is unsubstituted or substituted with 1-3 halo,
(e) $C_{3-6}$cycloalkyl, which is unsubstituted or substituted with 1-3 substituents each independently selected from:
(i) halo,
(ii) —O—$C_{1-6}$alkyl, which is unsubstituted or substituted with 1-6 halo, and
(iii) hydroxyl,
(f) —$NR^bR^c$,
(g) —C(=O)$NR^bR^c$,
(h) —$NR^b$—C(=O)$R^c$,
(i) —O—$CO_2R^d$,
(j) —$CO_2R^b$,
(k) —O—C(=O)$R^b$, and
(l) —OP(=O)$(OR^b)_2$, and
(3) phenyl or heterocycle wherein said heterocycle is selected from pyridyl, pyrimidinyl, thienyl, piperidinyl, azetidinyl, piperazinyl, pyrrolidinyl, morpholinyl, tetrahydrofuranyl, and pyrazinyl, which phenyl or heterocycle is unsubstituted or substituted with 1-3 substituents each independently selected from:
(a) halo,
(b) —CN,
(c) —O—$C_{1-4}$alkyl,
(d) hydroxyl, and
(e) —$C_{1-4}$alkyl, which is unsubstituted or substituted with 1-3 halo, and
(4) —$C_{3-6}$cycloalkyl.

In an embodiment of the present invention $11^a$ is independently selected from:
(1) hydrogen,
(2) $C_{1-4}$alkyl, which is unsubstituted or substituted with 1-3 substituents each independently selected from:
  (a) halo,
  (b) —O—$C_{1-4}$ alkyl,
  (c) hydroxyl,
  (d) phenyl,
  (e) $C_{3-6}$cycloalkyl,
  (f) —$NR^bR^c$,
  (g) —$CO_2R^b$, and
  (h) —OP(=O)(OR$^b$)$_2$, and
(3) phenyl or heterocycle wherein said heterocycle is selected from pyridyl, pyrimidinyl, piperidinyl, piperazinyl, pyrrolidinyl, and morpholinyl, and
(4) —$C_{3-6}$cycloalkyl.

In an embodiment of the present invention $R^b$ and $R^c$ are independently selected from:
(1) hydrogen,
(2) $C_{1-4}$alkyl, which is unsubstituted or substituted with 1-5 substituents each independently selected from:
  (a) halo,
  (b) hydroxyl,
  (c) —O—$C_{1-4}$alkyl, which is unsubstituted or substituted with 1-3 halo,
  (d) —$CO_2R^d$,
  (e) phenyl or heterocycle, wherein said heterocycle is selected from pyridyl, pyrimidinyl, piperidinyl, piperazinyl, pyrrolidinyl, morpholinyl, and tetrahydrofuranyl, which phenyl or heterocycle is unsubstituted or substituted with 1-3 substituents each independently selected from:
    (i) halo,
    (ii) —O—$C_{1-4}$alkyl, and
    (iii) —$C_{1-4}$alkyl, which is unsubstituted or substituted with 1-3 halo, and
(3) phenyl or heterocycle, wherein said heterocycle is selected from pyridyl, pyrimidinyl, thienyl, piperidinyl, azetidinyl, piperazinyl, pyrrolidinyl, morpholinyl, tetrahydrofuranyl, and pyrazinyl, which phenyl or heterocycle is unsubstituted or substituted with 1-3 substituents each independently selected from:
  (a) halo,
  (b) —O—$C_{1-4}$alkyl,
  (c) hydroxyl,
  (d) —$C_{1-4}$alkyl, which is unsubstituted or substituted with 1-3 halo, and
  (e) —$CO_2R^d$, and
(4) —$C_{3-6}$cycloalkyl.

In an embodiment of the present invention $R^b$ and $R^c$ are independently selected from:
(1) hydrogen,
(2) $C_{1-4}$alkyl, which is unsubstituted or substituted with 1-3 substituents each independently selected from:
  (a) halo,
  (b) hydroxyl,
  (c) —O—$C_{1-4}$alkyl,
  (d) $CO_2R^d$,
  (e) phenyl, which is unsubstituted or substituted with 1-3 substituents each independently selected from:
    (i) halo,
    (ii) —O—$C_{1-4}$alkyl, and
    (iii) —$C_{1-4}$alkyl, which is unsubstituted or substituted with 1-3 halo, and
(3) phenyl, which is unsubstituted or substituted with 1-3 substituents each independently selected from:
  (a) halo,
  (b) —O—$C_{1-4}$alkyl,
  (c) which is unsubstituted or substituted with 1-3 halo, and
  (d) —$CO_2R^d$, and
(4) —$C_3$cycloalkyl.

In an embodiment of the present invention $R^b$ and $R^c$ and the nitrogen to which they are attached join to form a 4-, 5-, or 6-membered ring optionally containing an additional heteroatom selected from N, O, and S, wherein the sulfur is optionally oxidized to the sulfone or sulfoxide.

In an embodiment of the present invention $R^d$ is independently selected from:
(1) $C_{1-4}$alkyl, which is unsubstituted or substituted with 1-3 substituents each independently selected from:
  (a) halo,
  (b) —O—$C_{1-4}$alkyl, which is unsubstituted or substituted with 1-3 halo,
  (c) hydroxyl,
  (d) —$CO_2$—$C_{1-4}$alkyl,
  (e) —$CO_2H$,
  (f) phenyl or heterocycle, wherein said heterocycle is selected from pyridyl, pyrimidinyl, piperidinyl, piperazinyl, pyrrolidinyl, morpholinyl, and tetrahydrofuranyl, which phenyl or heterocycle is unsubstituted or substituted with 1-3 substituents each independently selected from:
    (i) halo,
    (ii) —O—$C_{1-4}$alkyl,
    (iii) —$C_{1-4}$alkyl, which is unsubstituted or substituted with 1-3 halo, and
    (iv) hydroxyl,
(2) phenyl or heterocycle, wherein said heterocycle is selected from pyridyl, pyrimidinyl, thienyl, piperidinyl, azetidinyl, piperazinyl, morpholinyl, tetrahydrofuranyl, and pyrazinyl, which phenyl or heterocycle is unsubstituted or substituted with 1-3 substituents each independently selected from:
  (a) halo,
  (b) —O—$C_{1-4}$alkyl,
  (c) hydroxyl,
  (d) —$C_{1-4}$alkyl, which is unsubstituted or substituted with 1-3 halo,
  (e) —$C_{3-6}$cycloalkyl,
  (f) —$CO_2$—$C_{1-4}$alkyl, and
  (g) —$CO_2H$, and
(3) —$C_{3-6}$cycloalkyl.

In an embodiment of the present invention $R^d$ is independently selected from:
(1) $C_{3-4}$alkyl,
(2) phenyl, which is unsubstituted or substituted with 1-3 substituents each independently selected from:
  (a) halo,
  (b) —O—$C_{1-4}$alkyl, and
  (c) —$C_{1-4}$alkyl, which is unsubstituted or substituted with 1-3 halo, and
(3) —$C_{3-6}$cycloalkyl.

In one embodiment, the invention is directed to the compounds
{1-[1-({[(3R,6S)-6-(2,3-Difluorophenyl)-2-oxo-1-(2,2,2-trifluoroethyl)azepan-3-yl]amino}carbonyl)piperidin-4-yl]-2-oxo-1,2-dihydro-3H-imidazo[4,5-b]pyridin-3-yl}methyl dihydrogen phosphate (Example 1); and N-[(3R,6S)-6-(2,3-Difluorophenyl)-2-oxo-1-(2,2,2-trifluoroethyl)azepan-3-yl]-4-(3-methyl-2-oxo-2,3-dihydro-1H-imidazo[4,5-b]pyridin-1-yl)piperidine-1-carboxamide (Example 2);
or a pharmaceutically acceptable salt thereof.

Suitable salts for the compounds of the invention, such as for Example 1, include the sodium, potassium, magnesium and calcium salts.

As used herein, the term "alkyl," by itself or as part of another substituent, means a saturated straight or branched chain hydrocarbon radical having the number of carbon atoms designated (e.g., $C_{1-10}$ alkyl means an alkyl group having from one to ten carbon atoms). Preferred alkyl groups for use in the invention are $C_{1-6}$ alkyl groups, having from one to six carbon atoms. Exemplary alkyl groups include methyl, ethyl, n-propyl, isopropyl, n-butyl, isobutyl, tert-butyl, pentyl, hexyl, and the like.

As used herein, the term "cycloalkyl," by itself or as part of another substituent, means a saturated cyclic hydrocarbon radical having the number of carbon atoms designated (e.g., $C_{3-12}$ cycloalkyl means a cycloalkyl group having from three to twelve carbon atoms), The term cycloalkyl as used herein includes mono-, bi- and tricyclic saturated carbocycles, as well as bridged and fused ring carbocycles, such as Spiro fused ring systems.

Preferred cycloalkyl groups for use in the invention are monocyclic $C_{3-8}$ cycloalkyl groups, having from three to eight carbon atoms. Exemplary monocyclic cycloalkyl groups include cyclopropyl, cyclobutyl, cyclopentyl, cyclohexyl and the like. Exemplary bridged cycloalkyl groups include adamantly and norbornyl. Exemplary fused cycloalkyl groups include decahydronaphthalene.

The term "halo" or "halogen" includes fluoro, chloro, bromo and iodo.

As used herein, the term "heterocycle," by itself or as part of another substituent, means a saturated or unsaturated cyclic group having at least one ring heteroatom (O, N or S). The term "heterocycle" includes multiple ring systems as well as single ring systems. Exemplary heterocycle groups for use in the invention include pyridyl, pyrimidinyl, thienyl, pyridazinyl, piperidinyl, azetidinyl, furanyl, piperazinyl, pyrrolidinyl, morpholinyl, tetrahydrofuranyl, tetrahydropyranyl and pyrazinyl.

When a heterocyclic group as defined herein is substituted, the substituent may be bonded to a ring carbon atom of the heterocyclic group, or to a ring heteroatom (i.e., a nitrogen, oxygen or sulfur), which has a valence which permits substitution. Preferably, the substituent is bonded to a ring carbon atom. Similarly, when a heterocyclic group is defined as a substituent herein, the point of attachment may be at a ring carbon atom of the heterocyclic group, or on a ring heteroatom (i.e., a nitrogen, oxygen or sulfur), which has a valence which permits attachment. Preferably, the attachment is at a ring carbon atom.

Some of the compounds of the instant invention have at least one asymmetric center. Additional asymmetric centers may be present depending upon the nature of the various substituents on the molecule. Compounds with asymmetric centers give rise to enantiomers (optical isomers), diastereomers (configurational isomers) or both, and it is intended that all of the possible enantiomers and diastereomers in mixtures and as pure or partially purified compounds are included within the scope of this invention. The present invention is meant to encompass all such isomeric forms of these compounds.

Compounds described herein may contain one or more double bonds, and may thus give rise to cis/trans isomers as well as other conformational isomers. The present invention includes all such possible isomers as well as mixtures of such isomers.

As used herein, the term "prodrug" refers to a molecule that is inert, i.e. not pharmacologically active, but that has pharmacological activity upon activation by a biological system. For example, a prodrug is a compound which is inert when in a tablet, capsule or other pharmaceutical composition (such as in an injectable form), but is modified and becomes pharmacologically active in viva, upon ingestion by a mammal. Thus, compounds of formulas (I), (Ia) and (Ib) are modified in vivo to release compounds which are pharmacologically active as CGRP inhibitors (for example, in the treatment of migraine).

The phrase "pharmaceutically acceptable" is used herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

As used herein, "pharmaceutically acceptable salts" refer to derivatives wherein the parent compound is modified by making acid or base salts thereof. Examples of pharmaceutically acceptable salts include, but are not limited to, mineral or organic acid salts of basic residues such as amines; alkali or organic salts of acidic residues such as carboxylic acids; and the like. The pharmaceutically acceptable salts include the conventional non-toxic salts or the quaternary ammonium salts of the parent compound formed, for example, from non-toxic inorganic or organic acids. Suitable salts derived from organic or inorganic acids include the hydrochloride, hydrobromide, nitrate, phosphate, sulfate, carbonate, acetate, fumarate, tartrate, citrate, malate, succinate, lactate, stearate, propionate, benzoate, hippurate, maleate, gluconate, mesylate, tosylate, oleate, lactobionate, laurylsulphate, ascorbate, adipate, gluceptate, glutamate, glucoronate, besylate, caprylate, isetionate, gentisate, malonate, napsylate, edisylate, pamoate, xinafoate, napadisylate, oxalate, cinnamate, mandelate, undecylenate and camsylate.

Free bases and salts derived from inorganic bases include aluminum, ammonium, dimethylammonium, ethanolammonium, calcium, copper, ferric, ferrous, lithium, magnesium, manganic salts, manganous, potassium, sodium, zinc, and the like. Other suitable salts derived from cations include organic amines, such as lysine, arginine, tromethamine, benzathine, benethamine, meglumine, choline, epolamine, hydrabamine, ethylenediamine and imidazole.

It will be understood that, as used herein, references to the compounds of Formula I are meant to also include the pharmaceutically acceptable salts.

The subject compounds are useful as prodrugs in a method of antagonism of CGRP receptors in a patient such as a mammal in need of such antagonism comprising the administration of an effective amount of the compound. The present invention is directed to the use of the compounds disclosed herein as prodrugs of antagonists of CGRP receptors. In addition to primates, especially humans, a variety of other mammals can be treated according to the method of the present invention.

Another embodiment of the present invention is directed to a method for the treatment, control, amelioration, or reduction of risk of a disease or disorder in which the CGRP receptor is involved in a patient that comprises administering to the patient a therapeutically effective amount of a prodrug of an antagonist of CGRP receptors, such as a compound of formula (I).

The present invention is further directed to a method for the manufacture of a medicament for antagonism of CGRP receptors activity in humans and animals comprising combining a prodrug compound of the present invention with a pharmaceutical carrier or diluent.

The subject treated in the present methods is generally a mammal, for example a human being, male or female, in whom antagonism of CGRP receptor activity is desired. The term "therapeutically effective amount" means the amount of the subject compound that, as a prodrug, will elicit the biological or medical response of a tissue, system, animal or human that is being sought by the researcher, veterinarian, medical doctor or other clinician. As used herein, the term "treatment" refers both to the treatment and to the prevention or prophylactic therapy of the mentioned conditions, particularly in a patient who is predisposed to such disease or disorder.

The term "composition" as used herein is intended to encompass a product comprising the specified ingredients in the specified amounts, as well as any product which results, directly or indirectly, from combination of the specified ingredients in the specified amounts. Such term in relation to pharmaceutical composition, is intended to encompass a product comprising the prodrug of the invention, and the inert ingredient(s) that make up the carrier, as well as any product which results, directly or indirectly, from combination, complexation or aggregation of any two or more of the ingredients, or from dissociation of one or more of the ingredients, or from other types of reactions or interactions of one or more of the ingredients. Accordingly, the pharmaceutical compositions of the present invention encompass any composition made by admixing a compound of the present invention and a pharmaceutically acceptable carrier. By "pharmaceutically acceptable" it is meant the carrier, diluent or excipient must be compatible with the other ingredients of the formulation and not deleterious to the recipient thereof.

The compounds of the present invention have utility in treating, preventing, ameliorating, controlling or reducing the risk of one or more of the following conditions or diseases: headache; migraine; cluster headache; chronic tension type headache; pain; chronic pain; neurogenic inflammation and inflammatory pain; neuropathic pain; eye pain; tooth pain; diabetes; non-insulin dependent diabetes mellitus; vascular disorders; inflammation; arthritis; bronchial hyperreactivity, asthma; shock; sepsis; opiate withdrawal syndrome; morphine tolerance; hot flashes in men and women; allergic dermatitis; psoriasis; encephalitis; brain trauma; epilepsy; neurodegenerative diseases; skin diseases; neurogenic cutaneous redness, skin rosaceousness and erythema; inflammatory bowel disease, irritable bowel syndrome, cystitis; and other conditions that may be treated or prevented by antagonism of CGRP receptors. Of particular importance is the acute or prophylactic treatment of headache, including migraine and cluster headache.

The compounds of the present invention may be used in combination with one or more other drugs in the treatment, prevention, control, amelioration, or reduction of risk of diseases or conditions for which compounds of Formula I, Ia or Ib or the other drugs may have utility, where the combination of the drugs together are safer or more effective than either drug alone. Such other drug(s) may be administered, by a route and in an amount commonly used therefor, contemporaneously or sequentially with a compound of Formula I, Ia or Ib. When a compound of Formula I, Ia or Ib is used contemporaneously with one or more other drugs, a pharmaceutical composition in unit dosage form containing such other drugs and the compound of Formula I, Ia or Ib is preferred. However, the combination therapy may also include therapies in which the compound of Formula I, Ia or Ib and one or more other drugs are administered on different overlapping schedules. It is also contemplated that when used in combination with one or more other active ingredients, the compounds of the present invention and the other active ingredients may be used in lower doses than when each is used singly. Accordingly, the pharmaceutical compositions of the present invention include those that contain one or more other active ingredients, in addition to a compound of Formula I, Ia or Lb.

For example, the present compounds may be used in conjunction with an an anti-migraine agent, such as ergotamine and dihydroergotamine, or other serotonin agonists, especially a 5-$HT_{1B/1D}$ agonist, for example sumatriptan, naratriptan, zolmitriptan, eletriptan, almotriptan, frovatriptan, donitriptan, and rizatriptan, a 5-$HT_{1D}$ agonist such as PNU-142633 and a 5-$HT_{1F}$ agonist such as LY334370; a cyclooxygenase inhibitor, such as a selective cyclooxygenase-2 inhibitor, for example rofecoxib, etoricoxib, celecoxib, valdecoxib or paracoxib; a non-steroidal anti-inflammatory agent or a cytokine-suppressing anti-inflammatory agent, for example with a compound such as ibuprofen, ketoprofen, fenoprofen, naproxen, indomethacin, sulindac, meloxicam, piroxicam, tenoxicam, lornoxicam, ketorolac, etodolac, mefenamic acid, meclofenamic acid, flufenamic acid, tolfenamic acid, diclofenac, oxaprozin, apazone, nimesulide, nabumetone, tenidap, etanercept, tolmetin, phenylbutazone, oxyphenbutazone, diflunisal, salsalate, olsalazine or sulfasalazine and the like; or glucocorticoids. Similarly, the instant compounds may be administered with an analgesic such as aspirin, acetaminophen, phenacetin, fentanyl, sufentanil, methadone, acetyl methadol, buprenorphine or morphine.

Additionally, the present compounds may be used in conjunction with an interleukin inhibitor, such as an interleukin-1 inhibitor; an NK-1 receptor antagonist, for example aprepitant; an NMDA antagonist; an NR2B antagonist; a bradykinin-1 receptor antagonist; an adenosine A1 receptor agonist; a sodium channel blacker, for example lamotrigine; an opiate agonist such as levomethadyl acetate or methadyl acetate; a lipoxygenase inhibitor, such as an inhibitor of 5-lipoxygenase; an alpha receptor antagonist, for example indoramin; an alpha receptor agonist; a vanilloid receptor antagonist; a renin inhibitor; a granzyme B inhibitor; a substance P antagonist; an endothelin antagonist; a norepinephrine precursor; anti-anxiety agents such as diazepam, alprazolam, chlordiazepoxide and chlorazepate; serotonin 5$HT_2$ receptor antagonists; opiod agonists such as codeine, hydrocodone, tramadol, dextropropoxyphene and febtanyl; an mGluR5 agonist, antagonist or potentiator; a GABA A receptor modulator, for example acamprosate calcium; nicotinic antagonists or agonists including nicotine; muscarinic agonists or antagonists; a selective serotonin reuptake inhibitor, for example fluoxetine, paroxetine, sertraline, duloxetine, escitalopram, or citalopram; an antidepressant, for example amitriptyline, nortriptyline, clomipramine, imipramine, venlafaxine, doxepin, protriptyline, desipramine, trimipramine, or imipramine; a leukotriene antagonist, for example montelukast or zafirlukast; an inhibitor of nitric oxide or an inhibitor of the synthesis of nitric oxide.

Also, the present compounds may be used in conjunction with gap junction inhibitors; neuronal calcium channel blockers such as civamide; AMPA/KA antagonists such as LY293558; sigma receptor agonists; and vitamin B2.

Also, the present compounds may be used in conjunction with ergot alkaloids other than ergotamine and dihydroergotamine, for example ergonovine, methylergonovine, metergoline, ergoloid mesylates, dihydroergocornine, dihydroergocristine, dihydroergocryptine, dihydro-α-ergocryptine, dihydro-β-ergocryptine, ergotoxine, ergocornine, ergocristine, ergocryptine, α-ergocryptine, β-ergocryptine, ergosine, ergostane, bromocriptine, or methysergide.

Additionally, the present compounds may be used in conjunction with a beta-adrenergic antagonist such as timolol, propanolol, atenolol, metoprolol or nadolol, and the like; a MAO inhibitor, for example phenelzine; a calcium channel blocker, for example flunarizine, diltiazem, amlodipine, felodipine, nisolipine, isradipine, nimodipine, lomerizine, verapamil, nifedipine, or prochlorperazine; neuroleptics such as olanzapine, droperidol, prochlorperazine, chlorpromazine and quetiapine; an anticonvulsant such as topiramate, zonisamide, tonabersat, earabersat, levetiracetarn, lamotrigine, tiagabine, gabapentin, pregabalin or divalproex sodium; an anti-hypertensive such as an angiotensin II antagonist, for example losartan, irbesartin, valsartan, eprosartan, telmisartan, olmesartan, medoxomil, candesartan and candesartan cilexetil, an angiotensin I antagonist, an angiotensin converting enzyme inhibitor such as lisinopril, enalapril, captopril, benazepril, quinapril, perindopril, ramipril and trandolapril; or botulinum toxin type A or B.

The present compounds may be used in conjunction with a potentiator such as caffeine, an H2-antagonist, simethicone, aluminum or magnesium hydroxide; a decongestant such as oxymetazoline, epinephrine, naphazoline, xylometazoline, propylhexedrine, or levo-desoxy-ephedrine; an antitussive such as caramiphen, carbetapentane, or dextromethorphan; a diuretic; a prokinetic agent such as metoclopramide or domperidone; a sedating or non-sedating antihistamine such as acrivastine, azatadine, bromodiphenhydramine, brompheniramine, carbinoxamine, chlorpheniramine, clemastine, dexbrompheniramine, dexchlorpheniramine, diphenhydramine, doxylamine, loratadine, phenindamine, pheniramine, phenyltoloxamine, promethazine, pyrilamine, terfenadine, triprolidine, phenylephrine, phenylpropanolamine, or pseudoephedrine. The present compounds also may be used in conjunction with anti-emetics.

In a particularly preferred embodiment the present compounds are used in conjunction with an anti-migraine agent, such as: ergotamine or dihydroergotamine; a 5-$HT_1$ agonist, especially a 5-$HT_{1B/1D}$ agonist, in particular, sumatriptan, naratriptan, zolmitriptan, eletriptan, almotriptan, frovatriptan, donitriptan, avitriptan and rizatriptan, and other serotonin agonists; and a cyclooxygenase inhibitor, such as a selective cyclooxygenase-2 inhibitor, in particular, rofecoxib, etoricoxib, celecoxib, valdecoxib or paracoxib.

The above combinations include combinations of a compound of the present invention not only with one other active compound (or prodrug thereof), but also with two or more other active compounds (or prodrugs thereof). Likewise, compounds of the present invention may be used in combination with other drugs (or prodrugs thereof) that are used in the prevention, treatment, control, amelioration, or reduction of risk of the diseases or conditions for which compounds of the present invention are useful. Such other drugs may be administered, by a route and in an amount commonly used therefore, contemporaneously or sequentially with a compound of the present invention. When a compound of the present invention is used contemporaneously with one or more other drugs, a pharmaceutical composition containing such other drugs in addition to the compound of the present invention is preferred. Accordingly, the pharmaceutical compositions of the present invention include those that also contain one or more other active ingredients (or prodrug thereof), in addition to a compound of the present invention.

The weight ratio of the compound of the compound of the present invention to the other active ingredient(s) (or prodrugs thereof) may be varied and will depend upon the effective dose of each ingredient. Generally, an effective dose of each will be used. Thus, for example, when a compound of the present invention is combined with another agent, the weight ratio of the compound of the present invention to the other agent will generally range from about 1000:1 to about 1:1000, or from about 200:1 to about 1:200. Combinations of a compound of the present invention and other active ingredients (or prodrugs thereof) will generally also be within the aforementioned range, but in each case, an effective dose of each active ingredient should be used.

In such combinations the compound of the present invention and other active agents may be administered separately or in conjunction. In addition, the administration of one element may be prior to, concurrent to, or subsequent to the administration of other agent(s), via the same or different routes of administration.

The compounds of the present invention may be administered by oral, parenteral (e.g., intramuscular, intraperitoneal, intravenous, ICV, intracisternal injection or infusion, subcutaneous injection, or implant), by inhalation spray, nasal, vaginal, rectal, sublingual, or topical routes of administration and may be formulated, alone or together, in suitable dosage unit formulations containing conventional non-toxic pharmaceutically acceptable carriers, adjuvants and vehicles appropriate for each route of administration. In addition to the treatment of warm-blooded animals the compounds of the invention are effective for use in humans.

The pharmaceutical compositions for the administration of the compounds of this invention may conveniently be presented in dosage unit form and may be prepared by any of the methods well known in the art of pharmacy. All methods include the step of bringing the active ingredient (or prodrug thereof) into association with the carrier which constitutes one or more accessory ingredients. In general, the pharmaceutical compositions are prepared by uniformly and intimately bringing the active ingredient (or prodrug thereof) into association with a liquid carrier or a finely divided solid carrier or both, and then, if necessary, shaping the product into the desired formulation. In the pharmaceutical composition the active compound (or prodrug thereof) is included in an amount sufficient to produce the desired effect upon the process or condition of diseases. As used herein, the term "composition" is intended to encompass a product comprising the specified ingredients in the specified amounts, as well as any product which results, directly or indirectly, from combination of the specified ingredients in the specified amounts.

The pharmaceutical compositions containing the active ingredient (or prodrug thereof) may be in a form suitable for oral use, for example, as tablets, troches, lozenges, aqueous or oily suspensions, dispersible powders or granules, emulsions, solutions, hard or soft capsules, or syrups or elixirs. Compositions intended for oral use may be prepared according to any method known to the art for the manufacture of pharmaceutical compositions and such compositions may contain one or more agents selected from the group consisting of sweetening agents, flavoring agents, coloring agents and preserving agents in order to provide pharmaceutically elegant and palatable preparations. Tablets contain the active ingredient in admixture with non-toxic pharmaceutically acceptable excipients which are suitable for the manufacture of tablets. These excipients may be for example, inert diluents, such as calcium carbonate, sodium carbonate, lactose, calcium phosphate or sodium phosphate; granulating and disintegrating agents, for example, corn starch, or alginic acid; binding agents, for example starch, gelatin or acacia; and lubricating agents, for example magnesium stearate, stearic acid or talc. The tablets may be uncoated or they may be coated by known techniques to delay disintegration and absorption in the gastrointestinal tract and thereby provide a sustained action over a longer period. For example, a time delay material such as glyceryl monostearate or glyceryl distearate may be employed. They may also be coated by the techniques described in the U.S. Pat. Nos. 4,256,108; 4,160,452; and 4,265,874 to form osmotic therapeutic tablets for control release. Oral tablets may also be formulated for immediate release, such as fast melt tablets or wafers, rapid dissolve tablets or fast dissolve films.

Formulations for oral use may also be presented as hard gelatin capsules wherein the active ingredient (or prodrug thereof) is mixed with an inert solid diluent, for example, calcium carbonate, calcium phosphate or kaolin, or as soft gelatin capsules wherein the active ingredient (or prodrug thereof) is mixed with water or an oil medium, for example peanut oil, liquid paraffin, or olive oil.

Aqueous suspensions contain the active materials (or prodrugs thereof) in admixture with excipients suitable for the manufacture of aqueous suspensions. Such excipients are suspending agents, for example sodium carboxymethylcellulose, methylcellulose, hydroxy-propylmethylcellulose, sodium alginate, polyvinyl-pyrrolidone, gum tragacanth and gum acacia; dispersing or wetting agents may be a naturally-occurring phosphatide, for example lecithin, or condensation products of an alkylene oxide with fatty acids, for example polyoxyethylene stearate, or condensation products of ethylene oxide with long chain aliphatic alcohols, for example heptadecaethyleneoxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. The aqueous suspensions may also contain one or more preservatives, for example ethyl, or n-propyl, p-hydroxybenzoate, one or more coloring agents, one or more flavoring agents, and one or more sweetening agents, such as sucrose or saccharin.

Oily suspensions may be formulated by suspending the active ingredient (or prodrug thereof) in a vegetable oil, for example arachis oil, olive oil, sesame oil or coconut oil, or in a mineral oil such as liquid paraffin. The oily suspensions may contain a thickening agent, for example beeswax, hard paraffin or cetyl alcohol. Sweetening agents such as those set forth above, and flavoring agents may be added to provide a palatable oral preparation. These compositions may be preserved by the addition of an anti-oxidant such as ascorbic acid.

Dispersible powders and granules suitable for preparation of an aqueous suspension by the addition of water provide the active ingredient (or prodrug thereof) in admixture with a dispersing or wetting agent, suspending agent and one or more preservatives. Suitable dispersing or wetting agents and suspending agents are exemplified by those already mentioned above. Additional excipients, for example sweetening, flavoring and coloring agents, may also be present.

The pharmaceutical compositions of the invention may also be in the form of oil-in-water emulsions. The oily phase may be a vegetable oil, for example olive oil or arachis oil, or a mineral oil, for example liquid paraffin or mixtures of these.

Suitable emulsifying agents may be naturally-occurring gums, for example gum acacia or gum tragacanth, naturally-occurring phosphatides, for example soy bean, lecithin, and esters or partial esters derived from fatty acids and hexitol anhydrides, for example sorbitan monooleate, and condensation products of the said partial esters with ethylene oxide, for example polyoxyethylene sorbitan monooleate. The emulsions may also contain sweetening and flavoring agents.

Syrups and elixirs may be formulated with sweetening agents, for example glycerol, propylene glycol, sorbitol or sucrose. Such formulations may also contain a demulcent, a preservative and flavoring and coloring agents.

The compounds of the present invention may also be administered in the form of suppositories for rectal administration of the drug. These compositions can be prepared by mixing the drug with a suitable non-irritating excipient which is solid at ordinary temperatures but liquid at the rectal temperature and will therefore melt in the rectum to release the drug. Such materials are cocoa butter and polyethylene glycols.

For topical use, creams, ointments, jellies, solutions or suspensions and the like, containing the compounds of the present invention are used. Similarly, transdermal patches may also be used for topical administration.

The pharmaceutical composition and method of the present invention may further comprise other therapeutically active compounds (or prodrug thereof) as noted herein which are usually applied in the treatment of the above mentioned pathological conditions.

In a particular embodiment, the invention is directed to a sterile injectable aqueous or oleagenous suspension. This suspension may be formulated according to the known art using those suitable dispersing or wetting agents and suspending agents which have been mentioned above. The sterile injectable preparation may also be a sterile injectable solution or suspension in a non-toxic parenterally-acceptable diluent or solvent, for example as a solution in 1,3-butane diol. Among the acceptable vehicles and solvents that may be employed are water, Ringer's solution and isotonic sodium chloride solution. In addition, sterile, fixed oils are conventionally employed as a solvent or suspending medium. For this purpose any bland fixed oil may be employed including synthetic mono- or diglycerides. In addition, fatty acids such as oleic acid find use in the preparation of injectables.

The invention is also directed to a therapeutically effective intravenous formulation of the compounds of the invention, which is solution stable and isotonic with human blood. The intravenous formulation preferably can be packaged in plastic or glass, and meets government and compendial (USP in the US) particulate standards, and can be used as effective therapeutic agents.

The intravenous formulation may contain a buffer which can maintain the pH of the intravenous formulation within a desirable range. The buffering agent may maintain the intravenous formulation in an acceptable particulate profile for storage and subsequent use.

Pharmaceutical injectable formulations (such as subcutaneous formulations) will generally include a therapeutically effective amount of a compound of the invention, in addition to one or more pharmaceutically acceptable excipients. The compositions are advantageously prepared together with liquid inert carriers, such as water. Suitable liquid excipients/carriers are Water for Injection (US Pharmocoepia) and saline solution. The solution should be pyrogen-free, and also should be absent of particulate matter. Limits for the amount of particulate matter (i.e., extraneous, mobile undissolved substances, other than gas bubbles) which may be found in IV fluids are defined in the US Pharmacoepia.

Other suitable excipients and other additives include solvents such as ethanol, glycerol, propylene glycol, and mixtures thereof; stabilizers such as EDTA (ethylene diamine tetraacetic acid), citric acid, and mixtures thereof; antimicrobial preservatives, such as benzyl alcohol, methyl paraben, propyl paraben, and mixtures thereof; buffering agents, such as citric acid/sodium citrate, potassium hydrogen tartrate, sodium hydrogen tartrate, acetic acid/sodium acetate, maleic acid/sodium maleate, sodium hydrogen phthalate, phosphoric acid/potassium dihydrogen phosphate, phosphoric acid/disodium hydrogen phosphate, and mixtures thereat tonicity modifiers, such as sodium chloride, mannitol, dextrose, and mixtures thereof; fluid and nutrient replenishers such as synthetic amino acids, dextrose, sodium chloride, sodium lactate, Ringer's solution, and other electrolyte solutions.

The buffer system is generally a mixture of a weak acid and a soluble salt thereof, e.g., sodium citrate/citric acid; or the monocation or dication salt of a dibasic acid, e.g., potassium hydrogen tartrate; sodium hydrogen tartrate, phosphoric acid/potassium dihydrogen phosphate, and phosphoric acid/disodium hydrogen phosphate. The amount of buffer system used is dependent on the desired pH and the amount of the compound of the invention. The choice of appropriate buffer and pH of a formulation, depending on solubility of the drug to be administered, is readily made by a person having ordinary skill in the art.

In particular embodiments, the injectable formulation may be suitable for use with a needle-free injection device.

In the treatment, prevention, control, amelioration, or reduction of risk of conditions which require antagonism of CGRP receptor activity an appropriate dosage level will generally be about 0.01 to 500 mg per kg patient body weight per day which can be administered in single or multiple doses. A suitable dosage level may be about 0.01 to 250 mg/kg per day, about 0.05 to 100 mg/kg per day, or about 0.1 to 50 mg/kg per day. Within this range the dosage may be 0.05 to 0.5, 0.5 to 5 or 5 to 50 mg/kg per day. For oral administration, the compositions are may be provided in the form of tablets containing 1.0 to 1000 milligrams of the active ingredient, particularly 1, 5, 10, 15. 20, 25 50, 75, 100, 150, 200, 250, 300, 400, 500, 600, 750, 800, 900, and 1000 milligrams of the active ingredient for the symptomatic adjustment of the dosage to the patient to be treated. The compounds may be administered on a regimen of 1 to 4 times per day, or may be administered once or twice per day.

When treating, preventing, controlling, ameliorating, or reducing the risk of headache, migraine, cluster headache, or other diseases for which compounds of the present invention are indicated, generally satisfactory results are obtained when the compounds of the present invention are administered at a daily dosage of from about 0.1 milligram to about 100 milligram per kilogram of animal body weight, given as a single daily dose or in divided doses two to six times a day, or in sustained release form. For most large mammals, the total daily dosage is from about 1.0 milligrams to about 1000 milligrams, or from about 1 milligrams to about 50 milligrams. In the case of a 70 kg adult human, the total daily dose will generally be from about 7 milligrams to about 350 milligrams. This dosage regimen may be adjusted to provide the optimal therapeutic response.

It will be understood, however, that the specific dose level and frequency of dosage for any particular patient may be varied and will depend upon a variety of factors including the activity of the specific compound employed, the metabolic stability and length of action of that compound, the age, body weight, general health, sex, diet, mode and time of administration, rate of excretion, drug combination, the severity of the particular condition, and the host undergoing therapy.

The compounds of the present invention can be prepared readily according to the following Schemes and specific examples, or modifications thereof, using readily available starting materials, reagents and conventional synthesis procedures. In these reactions, it is also possible to make use of variants which are themselves known to those of ordinary skill in this art but are not mentioned in greater detail. The general procedures for making the compounds claimed in this invention can be readily understood and appreciated by one skilled in the art from viewing the following Schemes.

Several methods for preparing the compounds of this invention are illustrated in the following Schemes and Examples. Starting materials are made according to procedures known in the art or as illustrated herein.

In general, the compounds of the present invention may be obtained via derivatization of compound 1 (Scheme 1), which is described in Burgey et al. U.S. Pat. No. 6,953,790 B2. A specific example is illustrated in Scheme 1.

SCHEME 1

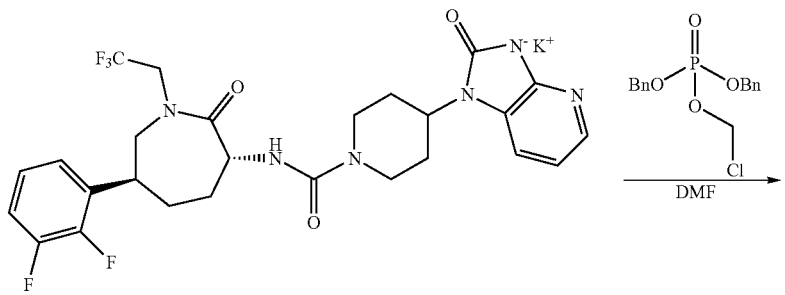

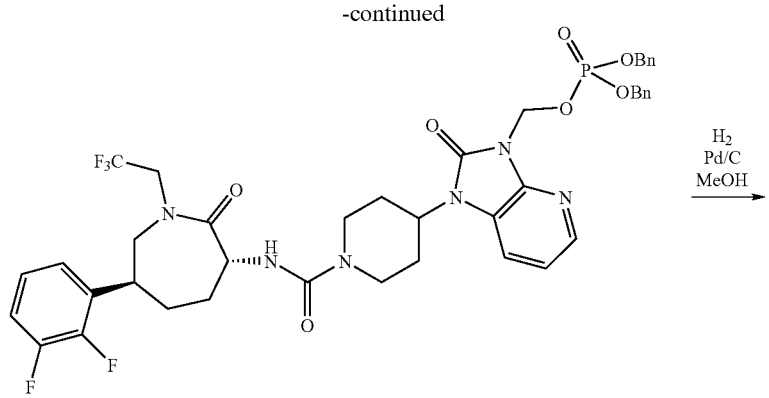

2

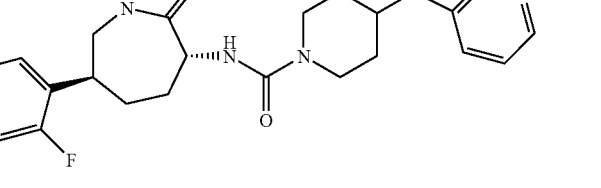

3

In Scheme 1, the potassium salt of compound 1 is treated with the known dibenzyl chloromethyl phosphate [Mäntylä et al. *Tetrahedron Lett.* 2002, 43, 3793] in DMF to provide the dibenzyl phosphate ester 2. Removal of the benzyl groups by catalytic hydrogenation leads to the desired product 3.

A route to another compound of interest, using a simple protecting group strategy, is illustrated in Scheme 2.

SCHEME 2

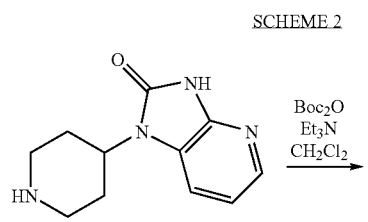

4

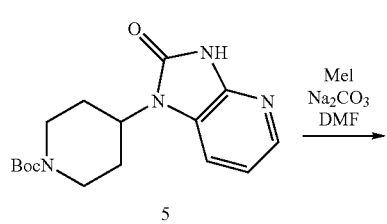

5

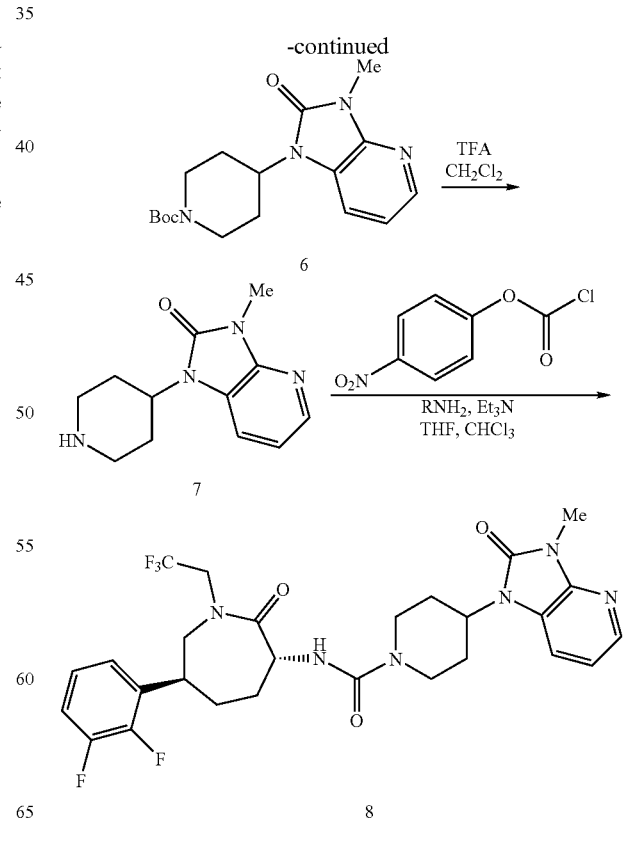

In Scheme 2, the known piperidine derivative 4 [Burgey et al. U.S. Pat. No. 6,953,790 B2] is converted to the corresponding tert-butyl carbamate 5. The azabenzimidazolone moiety in this protected intermediate may be alkylated with a variety of reagents to afford different derivatives. In Scheme 2, alkylation with iodomethane affords compound 6, which may be deprotected under acidic conditions to yield piperidine 7, Standard elaboration of this novel piperidine 7 may be carried out using the known (3R,6S)-3-amino-6-(2,3-difluorophenyl)-1-(2,2,2-trifluoroethyl)azepan-2-one [Burgey et al. U.S. Pat. No. 6,953,790 B2] and 4-nitrophenyl chloroformate to provide the desired product 8.

Other compounds of interest may be synthesized by modifications of the methodology described herein, as will be recognized by those skilled in the art of synthetic organic chemistry. For example, the use of other readily accessible alkylating or acylating agents may be used to provide alternatives to the analogues shown the foregoing schemes. Additionally, protection of the azabenzimidazolone moiety with a variety of protecting groups may facilitate reaction at the urea nitrogen to provide examples in which $R^2$ in formula I is not hydrogen.

In some cases the final product may be further modified, for example, by manipulation of substituents. These manipulations may include, but are not limited to, reduction, oxidation, alkylation, acylation, and hydrolysis reactions which are commonly known to those skilled in the art.

In some cases the order of carrying out the reactions in the foregoing schemes may be varied to facilitate the reaction or to avoid unwanted reaction products. Additionally, various protecting group strategies may be employed to facilitate the reaction or to avoid unwanted reaction products. The following examples are provided so that the invention might be more fully understood. These examples are illustrative only and should not be construed as limiting the invention in any way.

Example 1

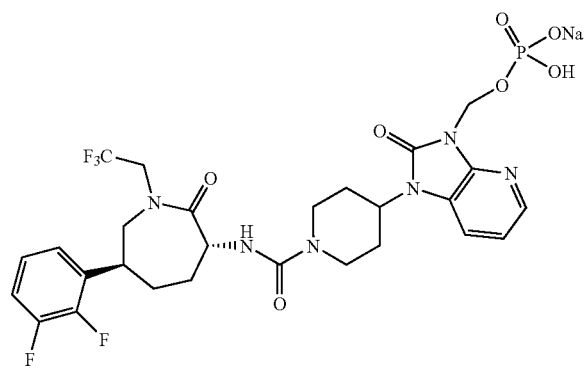

{1-[1-({[(3R,6S)-6-(2,3-Difluorophenyl)-2-oxo-1-(2,2,2-trifluoroethyl)azepan-3-yl]amino}carbonyl)piperidin-4-yl]-2-oxo-1,2-dihydro-3H-imidazo[4,5-b]pyridin-3-yl}methyl hydrogen sodium phosphate Step A. Dibenzyl {1-[1-({[(3R,6S)-6-(2,3-difluorophenyl)-2-oxo-1-(2,2,2-trifluoroethyl)azepan-3-yl]amino}carbonyl)piperidin-4-yl]-2-oxo-1,2-dihydro-3H-imidazo[4,5-b]pyridin-3-yl}methyl phosphate To a stirred solution of N-[(3R,6S)-6-(2,3-difluorophenyl)-2-oxo-1-(2,2,2-trifluoroethyl)azepan-3-yl]-4-(2-oxo-2,3-dihydro-1H-imidazo[4,5-b]pyridin-1-yl)piperidine-1-carboxamide, potassium salt, [Burgey et al. U.S. Pat. No. 6,953,790 B2] (1.00 g, 1.65 mmol) in anhydrous, degassed DMF (200 mL) at ambient temperature was added dibenzyl chloromethyl phosphate [Mäntylä et al. Tetrahedron Lett. 2002, 43, 3793] (0.54 g, 1.65 mmol). The resulting mixture was stirred at ambient temperature for 4 h, filtered, and purified by preparative HPLC on a C18 reversed phase column, eluting with a gradient of $H_2O:CH_3CN:CF_3CO_2H$—90:10:0.1 to 0:100:0.1. The product-containing fractions were poured into saturated aqueous $NaHCO_3$ and extracted with EtOAc (2×50 mL). The combined organic layers were dried over $Na_2SO_4$, filtered, and concentrated in vacuo to give the title compound. MS: m/z=857.7 (M+1).

Step B. {1-[1-({[(3R,6S)-6-(2,3-Difluorophenyl)-2-oxo-1-(2,2,2-trifluoroethyl)azepan-3-yl]amino}carbonyl)piperidin-4-yl]-2-oxo-1,2-dihydro-3H-imidazo[4,5-b]pyridin-3-yl}methyl hydrogen sodium phosphate A solution of dibenzyl {1-[1-({[(3R,6S)-6-(2,3-difluorophenyl)-2-oxo-1-(2,2,2-trifluoroethyl)azepan-3-yl]amino}carbonyl)piperidin-4-yl]-2-oxo-1,2-dihydro-3H-imidazo[4,5-b]pyridin-3-yl}methyl phosphate from Step A (530 mg, 0.619 mmol) in MeOH (15 mL) was hydrogenated using an H-Cube™ continuous flow reactor with 10% Pd/C as catalyst. The crude product was purified by preparative HPLC on a C18 reversed phase column, eluting with a gradient of $H_2O:CH_3CN:NH_4OH$—90:10:0.013 to 0:100:0. The product-containing fractions were lyophilized to give a white solid. The solid was dissolved in $H_2O$ and the acidic solution was adjusted to pH 7 by addition of 1 N NaOH and subjected to ion exchange chromatography using PRS (propyl sulfonic acid) cartridges and eluting with $H_2O$. The product-containing fractions were lyophilized to give the title compound. $^1$H NMR (DMSO-$d_6$) δ 7.98 (1H, d, J=5.1 Hz), 7.71 (1H, d, J=7.8 Hz), 7.34-7.26 (2H, m), 7.24-7.19 (1H, m), 7.04 (1H, dd, J=7.8, 5.1 Hz), 6.73 (1H, d, J=7.8 Hz), 5.49 (1H, d, J=4.2 Hz), 4.81 (1H, dd, J=11.4, 7.7 Hz), 4.53-4.45 (2H, m), 4.34-4.28 (1H, m), 4.19-4.08 (3H, m), 3.42-3.38 (1H, m), 3.04 (1H, t, J=10.5 Hz), 2.91 (1H, t, J=12.5 Hz), 2.85 (1H, t, J=12.2 Hz), 2.34-2.26 (1H, m), 2.13-2.03 (2H, m), 1.96 (2H, d, J=11.0 Hz), 1.75-1.68 (3H, m). MS: m/z=677.5 (M+1). HRMS: m/z=677.1906; calculated m/z=677.1907 for $C_{27}H_{31}F_5N_6O_7P$. Elemental analysis calculated for $C_{27}H_{29}F_5N_6O_7PNa\cdot0.85H_2O$: C, 45.43%; H, 4.34%; N, 11.77%. Found: C, 45.41%; H, 4.04%; N, 11.53%.

Example 2

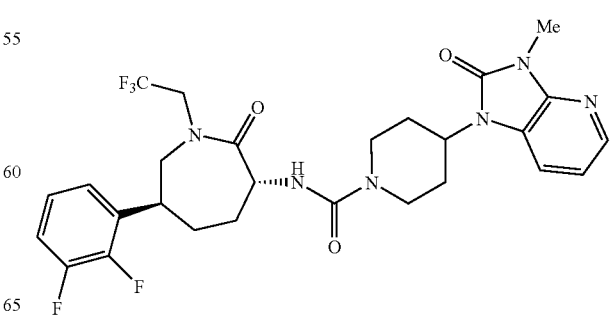

N-[(3R,6S)-6-(2,3-Difluorophenyl)-2-oxo-1-(2,2,2-trifluoroethyl)azepan-3-yl]-4-(3-methyl-2-oxo-2,3-dihydro-1H-imidazo[4,5-b]pyridin-1-yl)piperidine-1-carboxamide

Step A. tert-Butyl 4-(2-oxo-2,3-dihydro-1H-imidazo[4,5-b]pyridin-1-yl)piperidine-1-carboxylate To a stirred mixture of 1-piperidin-4-yl-1,3-dihydro-2H-imidazo[4,5-b]pyridin-2-one dihydrochloride [Burgey et al. U.S. Pat. No. 6,953,790 B2] (611 mg, 2.10 mmol) and di-tert-butyl dicarbonate (550 mg, 2.52 mmol) in $CH_2Cl_2$ (7 mL) at ambient temperature was added triethylamine (0.97 mL, 6.93 mmol). The resulting mixture was stirred at ambient temperature for 2 h then partitioned between $CH_2Cl_2$ (100 mL) and saturated aqueous $NaHCO_3$ (30 mL). The organic layer was washed with brine, dried over $Na_2SO_4$, filtered, and concentrated in vacuo. The crude product was purified by silica gel chromatography, eluting with a gradient of $CH_2Cl_2$:MeOH—100:0 to 95:5, to give the title compound. MS: m/z=319 (M+1).

Step B. tert-Butyl 4-(3-methyl-2-oxo-2,3-dihydro-1H-imidazo[4,5-b]pyridin-1-yl)piperidine-1-carboxylate To a stirred mixture of tart-butyl 4-(2-oxo-2,3-dihydro-1H-imidazo[4,5-b]pyridin-1-yl)piperidine-1-carboxylate from Step A (99 mg, 0.31 mmol) and sodium carbonate (73 mg, 0.68 mmol) in DMF (7 mL) at ambient temperature was added iodomethane (0.058 mL, 0.93 mmol). The resulting mixture was stirred at ambient temperature for 18 h then partitioned between $CH_2Cl_2$ (50 mL) and saturated aqueous $NaHCO_3$ (20 mL). The organic layer was washed with brine, dried over $Na_2SO_4$, filtered, and concentrated in vacuo. The crude product was purified by silica gel chromatography, eluting with a gradient of $CH_2Cl_2$:MeOH—100:0 to 95:5, to give the title compound. MS: m/z=333 (M+1).

Step C. 3-Methyl-1-piperidin-4-yl-1,3-dihydro-2H-imidazo[4,5-b]pyridin-2-one trifluoroacetate To a stirred solution of tert-butyl 4-(3-methyl-2-oxo-2,3-dihydro-1H-imidazo[4,5-b]pyridin-1-yl)piperidine-1-carboxylate from Step B (73 mg, 0.22 mmol) in $CH_2Cl_2$ (5 mL) was added trifluoroacetic acid (2 mL). The resulting mixture was stirred at ambient temperature for 1 h then concentrated in vacuo to give the title compound. MS: m/z=233 (M+1).

Step D. N-[(3R,6S)-6-(2,3-Difluorophenyl)-2-oxo-1-(2,2,2-trifluoroethyl)azepan-3-yl]-4-(3-methyl-2-oxo-2,3-dihydro-1H-imidazo[4,5-b]pyridin-1-yl)piperidine-1-carboxamide To a stirred solution of (3R,6S)-3-amino-6-(2,3-difluorophenyl)-1-(2,2,2-trifluoroethyl)azepan-2-one [Burgey et al. U.S. Pat. No. 6,953,790 B2] (16 mg, 0.050 mmol) in THF (8 mL) at 0° C. was added 4-nitrophenyl chloroformate (11 mg, 0.055 mmol) and triethylamine (0.015 mL, 0.11 mmol) and the resulting mixture was stirred at 0° C. for 1 h. A solution of 3-methyl-1-piperidin-4-yl-1,3-dihydro-2H-imidazo[4,5-b]pyridin-2-one trifluoroacetate from Step C (34 mg, 0.074 mmol) and triethylamine (0.042 mL, 0.30 mmol) in $CHCl_3$ (8 mL) was added and the resulting mixture was stirred at ambient temperature for 18 h then concentrated under reduced pressure. The residue was partitioned between $CH_2Cl_2$ (20 mL) and saturated aqueous $NaHCO_3$ (10 mL). The organic layer was washed with brine, dried over $Na_2SO_4$, filtered, and concentrated in vacuo. The crude product was purified by silica gel chromatography, eluting with a gradient of $CH_2Cl_2$:MeOH—100:0 to 95:5, to give the title compound. MS: m/z=581 (M+1). HRMS: m/z=581.2265; calculated m/z=581.2294 for $C_{27}H_{30}F_5N_6O_3$.

The compounds of the present invention may have improved aqueous solubility compared with telcagepant. For illustrative purposes, aqueous solubility data for telcagepant and Example 1 are shown in Table 1.

TABLE 1

| Compound | pH | Aqueous Solubility (mg/mL) |
|---|---|---|
| Telcagepant | 2.0 | 0.077 |
| Telcagepant | 7.3 | 0.031 |
| Example 1 | 4.0 | >150 |
| Example 1 | 9.0 | >150 |

The compounds of the present invention may be efficiently converted to give parent telcagepant in vivo. For illustrative purposes, data for the in vivo conversion of Example 1 to telcagepant in preclinical species are shown in Table 2.

TABLE 2

| Species | Compound Dosed (IV)[a] | IV Dose (μmol/kg) | AUC of Compound 1 (μM · h)[b] | Bioavailability (%)[c] |
|---|---|---|---|---|
| Rat | Telcagepant | 3.53 | 6.46 | — |
| Rat | Example 1 | 2.87 | 3.76 | 72 |
| Dog | Telcagepant | 0.88 | 1.18 | — |
| Dog | Example 1 | 0.88 | 1.20 | 102 |
| Rhesus | Telcagepant | 0.88 | 1.80 | — |
| Rhesus | Example 1 | 0.88 | 1.00 | 56 |

[a] Compounds dosed using DMSO vehicle.
[b] AUC in plasma determined using LC/MS analysis.
[c] Bioavailability of telcagepant following dosing with Example 1.

The following abbreviations are used throughout the text:
Me=methyl
MeOH=methanol
Et=ethyl
EtOAc=Ethyl Acetate
DMF: N,N'-dimethylformamide
rt=room temperature
hr=hour
min=minutes
M=molar
HPLC=high pressure liquid chromatography While the invention has been described and illustrated with reference to certain particular embodiments thereof, those skilled in the art will appreciate that various adaptations, changes, modifications, substitutions, deletions, or additions of procedures and protocols may be made without departing from the spirit and scope of the invention. It is intended, therefore, that the invention be defined by the scope of the claims that follow and that such claims be interpreted as broadly as is reasonable.

What is claimed is:

1. A compound of formula (I)

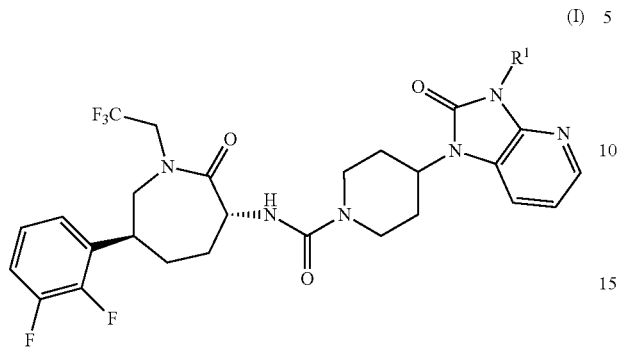

wherein:

$R^1$ is $C_{1-4}$alkyl, which is substituted with 1-7 substituents each independently selected from:
(a) —OP(=O)(OH)$_2$,
(b) —OP(=O)(OH)$R^a$, $R^a$ is independently selected from:
(1) hydrogen,
(2) $C_{1-6}$alkyl, which is unsubstituted or substituted with 1-7 substituents each independently selected from:
  (a) halo,
  (b) —O—$C_{1-6}$alkyl, which is unsubstituted or substituted with 1-6 halo,
  (c) hydroxyl,
  (d) —CN,
  (e) phenyl or heterocycle wherein said heterocycle is selected from pyridyl, pyrimidinyl, thienyl, pyridazinyl, piperidinyl, azetidinyl, furanyl, piperazinyl, pyrrolidinyl, morpholinyl, tetrahydrofuranyl, tetrahydropyranyl and pyrazinyl, which phenyl or heterocycle is unsubstituted or substituted with 1-3 substituents each independently selected from:
    (i) halo,
    (ii) —O—$C_{1-6}$alkyl, which is unsubstituted or substituted with 1-6 halo,
    (iii) —CN,
    (iv) nitro,
    (v) hydroxyl, and
    (vi) —$C_{1-6}$alkyl, which is unsubstituted or substituted with 1-6 halo,
  (f) $C_{3-6}$cycloalkyl, which is unsubstituted or substituted with 1-5 substituents each independently selected from:
    (i) halo,
    (ii) —O—$C_{1-6}$alkyl, which is unsubstituted or substituted with 1-6 halo,
    (iii) —CN,
    (iv) hydroxyl, and
    (v) —$C_{1-6}$alkyl, which is unsubstituted or substituted with 1-6 halo,
  (g) —N$R^bR^c$,
  (h) —S(O)$_vR^d$,
  (i) —C(=O)N$R^bR^c$,
  (j) —N$R^b$—C(=O)$R^c$,
  (k) —N$R^b$—SO$_2R^d$,
  (l) —O—CO$_2R^d$,
  (m) —O—(C=O)—N$R^bR^c$,
  (n) —N$R^b$—(C=O)—N$R^bR^c$,
  (o) —C(=O)$R^b$,
  (p) —CO$_2R^b$,
  (q) —O—C(=O)$R^b$,
  (r) —N$R^b$—CO$_2R^d$,
  (s) —N$R^b$—(C=N$R^b$)—N$R^bR^c$,
  (t) —CF$_3$,
  (u) —Si($C_{1-4}$alkyl)$_3$, and
  (v) —OP(=O)(O$R^b$)$_2$, and
(3) phenyl or heterocycle wherein said heterocycle is selected from pyridyl, pyrimidinyl, thienyl, pyridazinyl, piperidinyl, azetidinyl, furanyl, piperazinyl, pyrrolidinyl, morpholinyl, tetrahydrofuranyl, tetrahydropyranyl and pyrazinyl, which phenyl or heterocycle is unsubstituted or substituted with 1-3 substituents each independently selected from:
  (a) halo,
  (b) —CN,
  (c) —O—$C_{1-6}$alkyl, which is unsubstituted or substituted with 1-6 halo,
  (d) nitro,
  (e) hydroxyl, and
  (f) —$C_{1-6}$alkyl, which is unsubstituted or substituted with 1-6 halo, and
(4) —$C_{3-6}$cycloalkyl, which is unsubstituted or substituted with 1-6 halo;

$R^b$ and $R^c$ are independently selected from:
(1) hydrogen,
(2) $C_{1-6}$alkyl, which is unsubstituted or substituted with 1-7 substituents each independently selected from:
  (a) halo,
  (b) hydroxyl,
  (c) —O—$C_{1-6}$alkyl, which is unsubstituted or substituted with 1-6 halo,
  (d) —CN,
  (e) —CO$_2R^d$,
  (f) phenyl or heterocycle, wherein said heterocycle is selected from pyridyl, pyrimidinyl, thienyl, pyridazinyl, piperidinyl, azetidinyl, furanyl, piperazinyl, pyrrolidinyl, morpholinyl, tetrahydrofuranyl, tetrahydropyranyl and pyrazinyl, which phenyl or heterocycle is unsubstituted or substituted with 1-3 substituents each independently selected from:
    (i) halo,
    (ii) —O—$C_{1-6}$alkyl, which is unsubstituted or substituted with 1-6 halo,
    (iii) —$C_{1-6}$alkyl, which is unsubstituted or substituted with 1-6 halo, and
    (iv) hydroxyl,
(3) phenyl or heterocycle, wherein said heterocycle is selected from pyridyl, pyrimidinyl, thienyl, pyridazinyl, piperidinyl, azetidinyl, furanyl, piperazinyl, pyrrolidinyl, morpholinyl, tetrahydrofuranyl, tetrahydropyranyl and pyrazinyl, which phenyl or heterocycle is unsubstituted or substituted with 1-3 substituents each independently selected from:
  (a) halo,
  (b) —O—$C_{1-6}$alkyl, which is unsubstituted or substituted with 1-6 halo,
  (c) hydroxyl,
  (d) —$C_{1-6}$alkyl, which is unsubstituted or substituted with 1-6 halo,
  (e) —$C_{3-6}$cycloalkyl, which is unsubstituted or substituted with 1-6 halo,
  (f) —CN, and
  (g) —CO$_2R^d$,
(4) —$C_{3-6}$cycloalkyl, which is unsubstituted or substituted with 1-6 halo;

or $R^b$ and $R^c$ and the nitrogen to which they are attached join to form a 4-, 5-, or 6-membered ring optionally containing an additional heteroatom selected from N, O, and S, wherein the sulfur is optionally oxidized to the sulfone or sulfoxide, which ring is unsubstituted or substituted with 1-4 substituents each independently selected from:
  (a) halo,
  (b) —$OR^d$,
  (c) —$C_{1-6}$alkyl, which is unsubstituted or substituted with 1-6 halo, and
  (d) phenyl;
$R^d$ is independently selected from:
  (1) $C_{1-6}$alkyl, which is unsubstituted or substituted with 1-4 substituents each independently selected from:
    (a) halo,
    (b) —O—$C_{1-6}$alkyl, which is unsubstituted or substituted with 1-6 halo,
    (c) hydroxyl,
    (d) —$CO_2$—$C_{1-4}$-alkyl,
    (e) —$CO_2H$,
    (f) —CN, and
    (g) phenyl or heterocycle, wherein said heterocycle is selected from pyridyl, pyrimidinyl, thienyl, pyridazinyl, piperidinyl, azetidinyl, furanyl, piperazinyl, pyrrolidinyl, morpholinyl, tetrahydrofuranyl, tetrahydropyranyl and pyrazinyl, which phenyl or heterocycle is unsubstituted or substituted with 1-3 substituents each independently selected from:
      a) halo,
      b) —O—$C_{1-6}$alkyl, which is unsubstituted or substituted with 1-6 halo,
      c) —$C_{1-6}$alkyl, which is unsubstituted or substituted with 1-6 halo, and
      d) hydroxyl,
  (2) phenyl or heterocycle, wherein said heterocycle is selected from pyridyl, pyrimidinyl, thienyl, pyridazinyl, piperidinyl, azetidinyl, furanyl, piperazinyl, pyrrolidinyl, morpholinyl, tetrahydrofuranyl, tetrahydropyranyl and pyrazinyl, which phenyl or heterocycle is unsubstituted or substituted with 1-3 substituents each independently selected from:
    (a) halo,
    (b) —O—$C_{1-6}$alkyl, which is unsubstituted or substituted with 1-6 halo,
    (c) hydroxyl,
    (d) —$C_{1-6}$alkyl, which is unsubstituted or substituted with 1-6 halo,
    (e) —$C_{3-6}$cycloalkyl, which is unsubstituted or substituted with 1-6 halo,
    (f) —CN,
    (g) —$CO_2$—$C_{1-4}$alkyl, and
    (h) —$CO_2H$, and
  (3) —$C_{3-6}$cycloalkyl, which is unsubstituted or substituted with 1-6 halo;
v is 0, 1, or 2;
or a pharmaceutically acceptable salt thereof, and individual enantiomers and diastereomers thereof.

2. A compound of claim 1, which is {1-[1-({[(3R,6S)-6-(2,3-Difluorophenyl)-2-oxo-1-(2,2,2-trifluoroethyl)azepan-3-yl]amino}carbonyl)piperidin-4-yl]-2-oxo-1,2-dihydro-3H-imidazo[4,5-b]pyridin-3-yl}methyl dihydrogen phosphate;
or a pharmaceutically acceptable salt thereof.

3. The compound of claim 2, which is the sodium phosphate salt or the potassium phosphate salt.

4. A pharmaceutical composition comprising a compound of claim 1, or a pharmaceutically acceptable salt thereof, and a pharmaceutically acceptable carrier.

5. A method for treating migraine in a patient in need thereof comprising administering to the patient a therapeutically effective amount of a compound of claim 1 or a pharmaceutically acceptable salt thereof.

* * * * *